United States Patent [19]
Hulkenberg et al.

[11] Patent Number: 5,095,020
[45] Date of Patent: Mar. 10, 1992

[54] CYTOSTATIC BETA-CARBOLINES

[75] Inventors: Antonius Hulkenberg; Ineke Van Wijngaarden, both of Weesp, Netherlands

[73] Assignee: Duphar International Research B.V., Weesp, Netherlands

[21] Appl. No.: 397,859

[22] Filed: Aug. 24, 1989

[30] Foreign Application Priority Data

Aug. 29, 1988 [NL] Netherlands ............... 8802123

[51] Int. Cl.$^5$ ............... A61K 31/44; C07D 491/197
[52] U.S. Cl. ............... 514/287; 546/21; 546/64; 546/65
[58] Field of Search ............... 514/287; 546/64, 65, 546/21

[56] References Cited
U.S. PATENT DOCUMENTS 3,644,384  2/1972  Schulenberg ............... 546/64

Primary Examiner—David B. Springer
Assistant Examiner—Jacqueline Haley
Attorney, Agent, or Firm—Stevens, Davis, Miller & Mosher

[57] ABSTRACT

The invention relates to a group of new β-carbolines, their bio-isosteric benzofuran and benzothiophene analogues, and to the preparation of these compounds.

The new compounds can be represented by the formula

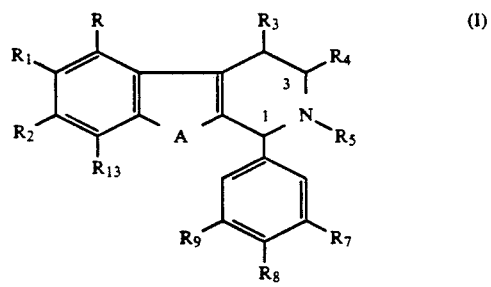

wherein
R, $R_1$ and $R_2$ are hydrogen, or R+$R_1$ or $R_1$+$R_2$ form a saturated heterocyclic ring having 5 or 6 ring atoms, which comprise 1 or 2 oxygen atoms;

$R_3$ is hydrogen, or hydroxy optionally derivatised with a sugar radical the 4,6-hydroxy groups of which are acetalised with an -ylidene group;

$R_4$ is a group of the formula —C($R_{11}$)$_2$—X—$R_{12}$, wherein the groups $R_{11}$ are hydrogen, or both groups $R_{11}$ together represent a double-bonded keto oxygen atom, X is oxygen or a group N$R_{14}$, wherein $R_{14}$ is hydrogen or alkyl having 1–4 C-atoms, and $R_{12}$ is hydrogen, alkyl having 1–4 C-atoms, alkanoyl having 1–4 C-atoms, the carbamoyl group or mono- or dialkylcarbamoyl group having 1–4 C-atoms per alkyl group;

$R_5$ is hydrogen, alkanoyl or alkyl having 1–4 C-atoms, or $R_4$+$R_5$ together form a group of the formula —C($R_{11}$)$_2$—X—Z, wherein $R_{11}$ and X have the above-mentioned meanings and Z is bound to the ring nitrogen atom and is a group

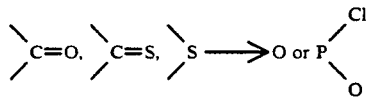

$R_7$ and $R_9$ independently of each other are hydrogen or alkoxy having 1–4 C-atoms, trifluoromethyl or halogen;

$R_8$ is hydrogen, alkoxy or alkanoyloxy having 1–4 C-atoms, hydroxy, halogen, benzyloxy, or $R_8$ and $R_9$ together constitute a dioxyalkylidene bridge;

A is oxygen, sulphur or a group

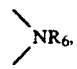

and $R_6$ and $R_{13}$ independently of each other are hydrogen or methyl, or, when A is nitrogen, $R_6$ and $R_{13}$ together may form a ring having 5–7 C-atoms. The compounds have good cytostatic properies.

3 Claims, No Drawings

CYTOSTATIC BETA-CARBOLINES

The invention relates to a group of new β-carbolines, their bio-isosteric benzofuran and benzothiophene analogues, to the preparation thereof, and to pharmaceutical compositions which comprise at least one of the said compounds as an active substance.

It has been found that β-carbolines, their bio-isosteric benzofuran and benzothiophene analogues of the general formula

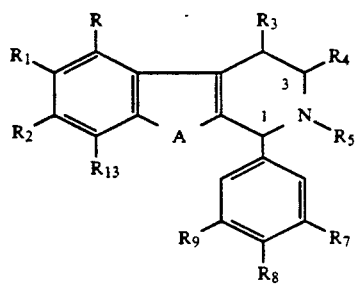

(I)

wherein

R, $R_1$ and $R_2$ are hydrogen, or $R+R_1$ or $R_1+R_2$ form a saturated heterocyclic ring having 5 or 6 ring atoms, which comprise 1 or 2 oxygen atoms;

$R_3$ is hydrogen, or hydroxy optionally derivatised with a sugar radical the 4,6-hydroxy groups of which are acetalised with an -ylidene group;

$R_4$ is a group of the formula $-C(R_{11})_2-X-R_{12}$, wherein the groups $R_{11}$ are hydrogen, or both groups $R_{11}$ together represent a double-bonded keto oxygen atom, X is oxygen or a group $NR_{14}$, wherein $R_{14}$ is hydrogen or alkyl having 1-4 C-atoms, and $R_{12}$ is hydrogen, alkyl having 1-4 C-atoms, alkanoyl having 1-4 C-atoms, the carbamoyl group or mono- or dialkylcarbamoyl group having 1-4 C-atoms per alkyl group;

$R_5$ is hydrogen, alkanoyl or alkyl having 1-4 C-atoms, or $R_4+R_5$ together form a group of the formula $-C(R_{11})_2-X-Z$, wherein $R_{11}$ and X have the abovementioned meanings and Z is bound to the ring nitrogen atom and is a group

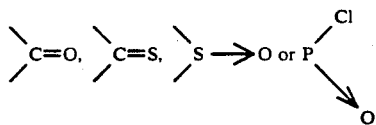

and $R_7$ and $R_9$ independently of each other are hydrogen or alkoxy having 1-4 C-atoms, trifluoromethyl or halogen;

$R_8$ is hydrogen, alkoxy or alkanoyloxy having 1-4 C-atoms, hydroxy, halogen, benzyloxy, or $R_8$ and $R_9$ together constitute a dioxyalkylidene bridge;

A is oxygen, sulphur or a

$R_6$ and $R_{13}$ independently of each other are hydrogen or methyl, or, when A is nitrogen, $R_6$ and $R_{13}$ together may form a ring having 5-7 C-atoms.

have very good cytostatic properties.

Examples of sugar radicals with which a hydroxyl group $R_3$ may be derivatised are glucoside and -ylidene glucosides, for example, benzylidene glucoside, thienylidene glucoside and ethylidene glucoside.

When in formula (I) one or more optically active carbon atoms are present, both the individual enantiomers and mixtures thereof belong to the invention.

Both the individual cis-isomers and trans-isomers and mixtures thereof belong to the invention.

The invention also relates to the acid addition salts and to prodrugs of the compounds of formula (I). Prodrugs are to be understood to mean compounds which as such are inactive and which after administration into the body are converted into an active compound of formula (I).

Suitable acids with which the compounds of formula (I) to be considered therefor can form pharmaceutically acceptable acid addition salts are, for example, hydrochloric acid. sulphuric acid, phosphoric acid, nitric acid, and organic acids, for example, citric acid; fumaric acid, maleic acid, tartaric acid, acetic acid, benzoic acid, p-toluene sulphonic acid, methane sulphonic acid and naphthalene sulphonic acid.

The compounds according to the invention, their acid addition salts and prodrugs can be processed, by means of standard techniques, to compositions for example, pills, tablets, coated tablets, capsules, powders, injection liquids, and the like, while using auxiliary substances suitable for this purpose, for example, solid and liquid carriar materials.

The new compounds according to the invention can be obtained in a manner known for the synthesis of this type of compounds, for example, by means of Bischler-Napieralski (method A) or Pictet Spengler (method B) reactions.

In the reaction schemes and tables hereinafter the following symbols have the indicated meaning:

$Z_1$ is the group of formula

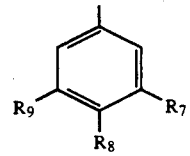

wherein $R_7$-$R_9$ have the above-mentioned meanings;

$Z_2$ is the group of formula

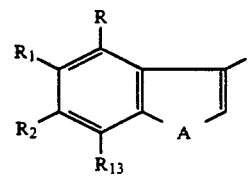

wherein R, $R_1$, $R_2$ and $R_{13}$ have the above-mentioned meanings, and A is oxygen, sulphur or a group 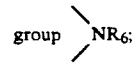

$Z_3$ is a group of the formula

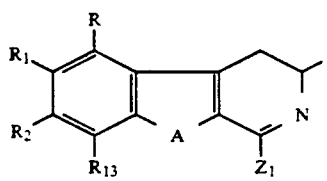

wherein R, $R_1$, $R_2$, $R_{13}$ and $Z_1$ have the above-mentioned meanings, and A is oxygen or sulphur;
$Z_4$ is a group of the formula

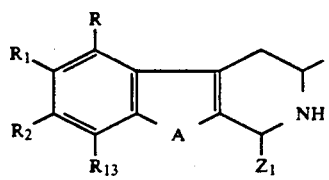

wherein R, $R_1$, $R_2$, $R_{13}$ and $Z_1$ have the above-mentioned meanings, and A is oxygen or sulphur or

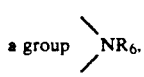

a group $\diagdown NR_6 \diagup$.

wherein $R_6$ has the above mentioned meaning;
$Z_5$ is the 3,4,5-trimethoxyphenyl group;
$Z_6$ is the 3,5-dimethoxyphenyl group
$Z_7$ is the 4-chlorophenyl group
$Z_8$ is the 3,4-dimethoxyphenyl group
$Z_9$ is the 4-hydroxy-3,5-dimethoxyphenyl group
$Z_{10}$ is the 3-methoxy-4,5-methylenedioxyphenyl group
$Z_{11}$ is the 3-methoxyphenyl group
$Z_{12}$ is the phenyl group
$Z_{13}$ is the 3-trifluoromethylphenyl group
$Z_{14}$ is the 3,5-dimethoxy-4-benzyloxyphenyl group.

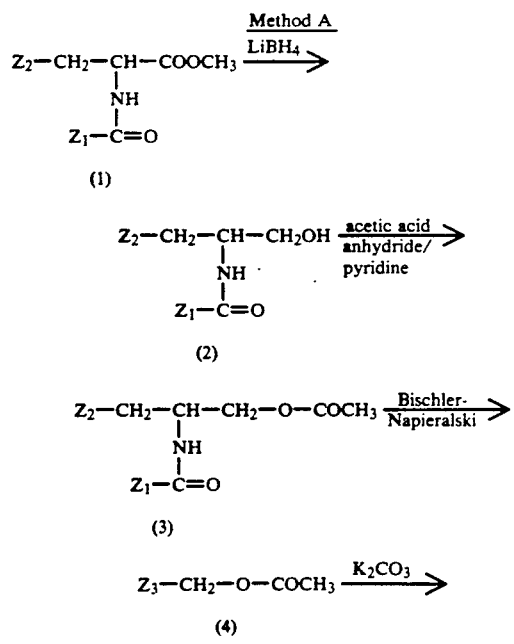

-continued
Method A

Starting compounds (1) can be obtained in a manner known per se by reaction of a compound (1a) with (1b);

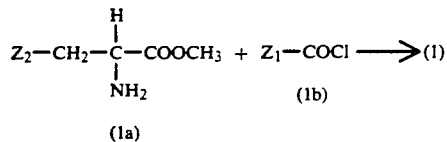

The compounds (1a) and (1b) are known compounds or can be obtained analogously to known compounds.

The reaction steps are carried out under conditions conventionally used for this type of reaction.

The so obtained compounds (5) can be converted in a manner known per se into compounds of formula I, wherein $R_5$ has the above-mentioned meanings a) by hydrogenating the double bond, for example, with $AlCl_3$ and $LiAlH_4$ (or by a catalytic reduction of a salt of (5)), or b) by reducing a quarternary derivative of compound (5) with $NaBH_4$ to obtain the trans-isomer.

Method B.

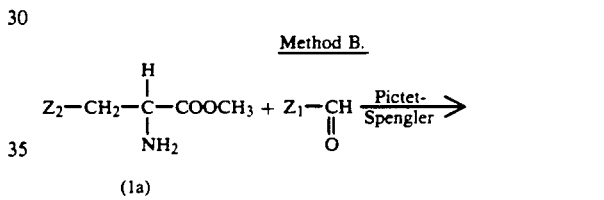

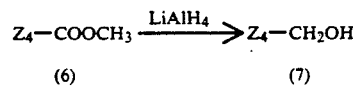

If desired, a substituent $R_5$ may be introduced in a manner known per se in the compounds (7) to be obtained in these manners.

The final products of formulae (5) and (7), respectively, to be obtained according to methods A and B may be converted in a manner known per se, for example with phosgene, thionylchloride or phosphoroxy trichloride into compounds of formula I according to the invention, wherein $R_4+R_5$ represent a group of the formula $-C(R_{11})_2-X-Z$, wherein $R_{11}$, X and Z have the above-mentioned meanings.

The cytostatic activity of the compounds according to the invention was tested in two in vitro tests.

1. Human cell line cytotoxicity

A number of representative compounds of the group according to the invention has been tested for cytotoxicity in at least five of the following human tumour cell lines: bladder T24, melanoma IGR37, breast MCF7, osteosarcoma A204, colon WIDR, HT29 and SW116 (P. P. Dendy and B. R. Hill, Human Tumour Drug, Sensitivity testing in vitro, Academic Press, 1983; H. B. Lamberts et al, Oncology 40, (1983), pp. 301-304; A. A. van der Huizen, Aziridinyl cyclophophazenes, synthesis, structure and cytostatic activity, thesis (1984), Groningen).

Procedure

Cells are provided on 24-well cluster plates in a quantity of $10^5$ cells/ml of medium After incubation at 37° C. for 24 hours in an atmosphere of air with 5% of $CO_2$, a suspension of the compound to be tested in 0.5 of CMC/salt solution is added to a final concentration of 15/ug/ml.

Adriamycin is used as a positive control compound. After incubation for 72 hours in the presence of the compound to be tested the cell layers are washed with a phosphatebuffered saline solution and the cells are coloured with crystal violet. The cell growth inhibition is estimated with reference to the coloured cells and expressed as follows:

4 approximately 100% cell growth inhibition
3 approximately 75% cell growth inhibition
2 approximately 50% cell growth inhibition
1 approximately 25% cell growth inhibition
0 no cell growth inhibition 2. Clonogenic test with human cell lines A number of compounds according to the invention has been tested in the so-called clonogenic test (R. Ludwig et al, Cancer Chemother. Pharmacol. 12, (1984), pp, 135-141; W. I. Schaefer and K. Friend, Cancer Letters, 1, (1976), pp. 259-262; P. P. Dendy and B. T. Hill, Human Tumour Drug, Sensitivity testing in vitro, Academic Press 1983). The following human cell lines are used: breast MCF7 and HTB26, color WIDR and HTB38, lung HTB53, melanoma HTB66, and uterus HTB114.

Cisplatinum, 5-fluorouracil, daunomycin, bleomycin and adrismycin are used as comparative substances.

Procedure

Each cell line is provided in a quantity of approximately $10^2$–$10^5$ cells/dish and incubated in an atmosphere of air with 5% of $CO_2$ at 37° C. The compound to be investigated is added, during providing the cells or after a pre-incubation on period of one night, as a solution or suspension in 0.5% of CMC/salt solution to a final concentration of 15/ug/ml.

The duration of the treatment is approximately three times the cell division cycle. The cells are then fixed, coloured and evaluated for the presence of colonies. The colony formation is expressed in the number of colonies which is present on the treated dishes as a percentage of the number of colonies which is present on control dishes The activity of a number of compounds I according to the invention is recorded in Tables A and B hereinafter as determined in test method 1.

TABLE A

| comp. no. | $R_1$ | $R_2$ | $R_3$ | R | Q | A | 3-D/L | 1,3-cis/ trans | m.p. (°C.) | cytotoxicity |
|---|---|---|---|---|---|---|---|---|---|---|
| 1 | H | H | H | $Z_5$ | $CONH_2$ | N | DL | cis | 256 | 1-4 |
| 2 | —$(CH_2)_3$— | | H | $Z_5$ | $COOCH_3$ | N | DL | cis | 140 | 0-4 |
| 3 | H | H | H | $Z_9$ | $CONH_2$ | N | DL | cis | >250 | 0-3 |
| 4 | H | H | H | $Z_6$ | $CONH_2$ | N | D | cis | 125 | 4-4 |
| 5 | H | H | H | $Z_7$ | $CONH_2$ | N | D | cis | 126 | 0-2 |
| 6 | H | H | H | $Z_8$ | $CONH_2$ | N | D | cis | 129 | 0-4 |
| 7 | H | H | H | $Z_5$ | $CH_2OH$ | N | DL | cis | 190 | 0-4 |
| 8 | H | H | H | $Z_5$ | $CH_2OH$ | N | D | cis | 212 | 4-4 |
| 9 | —$(CH_2)_3$— | | H | $Z_5$ | $CH_2OH$ | N | DL | cis | 188 | 0-2 |
| 10 | H | H | 6,7-O$(CH_2)_2$O | $Z_5$ | $CH_2OH$ | N | DL | cis | 135 | 0-4 |
| 11 | H | H | H | $Z_6$ | $CH_2OH$ | N | D | cis | 125 | 4-4 |
| 12 | H | $CH_3$ | H | $Z_5$ | $CH_2OH$ | N | D | cis | >60 | 3-4 |
| 13 | H | H | 5,6-O$(CH_2)_2$O— | $Z_5$ | $CH_2OH$ | N | DL | cis | 225 | 2-3 |
| 14 | H | H | H | $Z_5$ | $CONH_2$ | N | D | cis | 147 | 4-4 |
| 15 | H | H | H | $Z_5$ | $CONH_2$ | N | L | trans | 126 | 0-4 |
| 16 | H | H | H | $Z_5$ | $CH_2OH$ | N | L | trans | 102 | 0-4 |
| 17 | H | — | H | $Z_5$ | $CH_2OH$ | S | DL | cis | 163 | 4-4 |
| 18 | H | — | H | $Z_5$ | $CH_2OH$ | S | DL | trans | 148 | 4-4 |
| 19 | H | — | H | $Z_5$ | $CH_2OH$ | O | DL | cis | 188 | 4-4 |
| 20 | H | — | H | $Z_5$ | $CH_2OH$ | O | DL | trans | 151 | 3-4 |
| 21 | H | H | H | $Z_6$ | $CH_2OH$ | N | L | trans | 65 | 2-4 |

TABLE B

| comp. no. | $R_1$ | $R_2$ | $R_3$ | R | A | X—Y | 3-D/L | 1-3 cis/ trans | m.p. (°C.) | cytotox. |
|---|---|---|---|---|---|---|---|---|---|---|
| 22 | H | H | H | $Z_5$ | N | O—C=O | | DL | cis | 163 | 2-4 |

TABLE B-continued

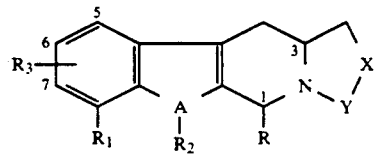

| comp. no. | R₁ | R₂ | R₃ | R | A | X—Y | 3-D/L | 1-3 cis/trans | m.p. (°C.) | cyto-tox. |
|---|---|---|---|---|---|---|---|---|---|---|
| 23 | H | H | H | $Z_5$ | N | O—S→O[1] | DL | cis | 235 | 3–4 |
| 24 | H | H | H | $Z_5$ | N | O—S→O[1] | DL | cis | 213 | 3–4 |
| 25 | H | H | H | $Z_5$ | N | O—C=O | D | cis | 135 | 4–4 |
| 26 | —(CH₂)₃— | | H | $Z_5$ | N | O—C=O | DL | cis | 223 | 2–4 |
| 27 | H | H | 6,7-O(CH₂)₂O— | $Z_5$ | N | O—C=O | DL | cis | 170 | 3–4 |
| 28 | H | H | 5,6-O(CH₂)₂O— | $Z_5$ | N | O—C=O | DL | trans | 120 | 4–4 |
| 29 | H | H | 5,6-O(CH₂)₂O— | $Z_5$ | N | O—C=O | DL | cis | 165 | 2–4 |
| 30 | H | H | H | $Z_5$ | N | O—S→O[1] | D | cis | 204 | 4–4 |
| 31 | H | H | H | $Z_5$ | N | O—S→O[1] | D | cis | 179 | 4–4 |
| 32 | H | H | H | $Z_7$ | N | O—S→O[1] | D | cis | 96 | 0–2 |
| 33 | H | H | H | $Z_7$ | N | O—S→O[1] | D | cis | oil | 2–4 |
| 34 | H | H | H | $Z_6$ | N | O—C=O | D | cis | 226 | 4–4 |
| 35 | H | H | H | $Z_8$ | N | O—C=O | D | cis | 151 | 0–4 |
| 36 | H | H | H | $Z_5$ | N | O—C=O | L | trans | 170 | 4–4 |
| 37 | H | H | H | $Z_9$ | N | O—C=O | D | cis | 159 | 4–4 |
| 38 | H | H | H | $Z_9$ | N | O—C=O | D | trans | 167 | 4–4 |
| 39 | H | H | H | $Z_5$ | N | O—P→O[1] / Cl | D | cis | 222 | 3–4 |
| 40 | H | H | H | $Z_5$ | N | O—P→O[1] / Cl | D | cis | 199 | 3–4 |
| 41 | H | H | H | $Z_5$ | N | O—C=O | D | trans | 183 | 0–2 |
| 42 | H | H | H | $Z_5$ | N | NH—C=O | L | trans | 145 | 4–4 |
| 43 | H | H | H | $Z_{10}$ | N | O—C=O | L | trans | 216 | 4–4 |
| 44 | H | H | H | $Z_{11}$ | N | O—C=O | L | trans | 208 | 4–4 |
| 45 | H | H | H | $Z_6$ | N | O—C=O | L | trans | 200 | 4–4 |
| 46 | H | H | H | $Z_{11}$ | N | O—C=O | D | cis | 207 | 4–4 |
| 47 | H | CH₃ | H | $Z_5$ | N | O—C=O | D | cis | 210 | 4–4 |
| 48 | H | H | H | $Z_6$ | N | O—S→O[1] | L | trans | 170 | 4–4 |
| 49 | H | H | H | $Z_6$ | N | O—S→O[1] | L | trans | 144 | 4–4 |
| 50 | H | — | H | $Z_5$ | S | O—C=O | DL | trans | 260 | 4–4 |
| 51 | H | — | H | $Z_5$ | S | O—C=O | DL | cis | 298 | 4–4 |
| 52 | H | H | H | $Z_{12}$ | N | O—C=O | L | trans | 257 | 4–4 |
| 53 | H | H | H | $Z_{13}$ | N | O—C=O | L | trans | >230 | 4–4 |
| 54 | H | H | H | $Z_{14}$ | N | O—C=O | L | trans | 106 | 4–4 |
| 55 | H | H | H | $Z_9$ | N | O—C=O | L | trans | 171 | 2–4 |
| 56 | H | H | H | $Z_6$ | N | NH—C=O | L | trans | 191 | 4–4 |
| 57 | H | H | H | $Z_6$ | N | NH—C=S | L | trans | 204 | 4–4 |
| 58 | H | — | H | $Z_5$ | O | O—C=O | DL | cis | 246 | 4–4 |
| 59 | H | — | H | $Z_5$ | O | O—C=O | DL | trans | 260 | 4–4 |
| 60 | H | H | H | $Z_5$ | N | O—C=S | L | trans | 249 | 4–4 |

[1] pair of stereoisomers

EXAMPLE I 15 g Of (R)-1-(3,4,5-trimethoxyphenyl)-3-carbomethoxy$\beta$-carboline were dissolved in 75 ml of dry tetrahydrofuran (THF). This solution was added dropwise to a suspension of 3.8 g of lithiumaluminium hydride in 50 ml of dry THF at a temperature below 10° C. The solution was then stirred at room temperature for 2.5 hours. After cooling again to 5°–10° C. 3.8 ml of water, 7.6 ml of 2N NaOH and 7.6 ml of water were added dropwise successivly. After stirring at room temperature for 1 hour the precipitate was sucked off and the filtrate was evaporated. The residue was recrystallised from ethyl acetate. Yield 8 g of compound 8 of Table A (pure 1,3-cis) having a melting-point of 212° C. $[\alpha]_D^{25} = 13.25$ (methanol).

Example II 0.7 ml Of triethylamine were added at 0° C. to a solution of 184 m; of 3-hydroxymethyl-1,2,3,4-tetrahydro-1-(3,4,5-trimethoxyphenyl)-β-carboline in 5 ml of dichloromethane. 0.7 ml Of a 1M solution of phosgene in dichloromethane were added dropwise likewise at 0° C. After stirring at 0° C. for 30 minutes ice water was added. The organic layer was separated and washed with 2N HCl and with water. The organic layer was dried with MgSO4, filtered and evaporated to dryness. The resulting brown residue was treated with 50 ml of ether and the precipitate was filtered off. Yield 140 mg of compound 22 (Table B) as a pale brown solid Melting-point 163° C.

EXAMPLE III 1 ml Of triethylamine was added to a solution of 840 mg of 3-hydroxymethyl-1-(3,4,5-trimethoxyphenyl)-1,2,3,4-tetrabydro-β-carboline in 10 ml of dichloromethane. 0.2 ml Of thionylchloride were then added dropwise at 0° C. and the mixture was stirred at room temperature for 18 hours. 50 ml Of water were added and extraction was carried out twice with 75 ml of dichloromethane. The organic layer was washed with 50 ml of 2N HCl and with 50 ml of water. After drying with MgSO4, filtering and evaporating to dryness the residue was separated by means of flash chromatography with 25% of ether/petroleum ether 60-80 as an eluent. In this manner two fractions were obtained.

Fraction I: 280 mg of white solid; melting-point 235° C. The proton in 3-position and the group S-O are trans with respect to each other (compound No. 23).

Fraction II: 190 mg of light-brown substance; melting-point 213° C. The proton in 3-position and the group S-O are cis with respect to each other (compound No 24, Table B).

EXAMPLE IV 1 g Of 3-carbomethoxy-1,2,3,4-tetrahydro-1-(3,4,5-trimethoxyphenyl)-β-carboline was added to 25 ml of methanol (saturated with NH3). The mixture was stirred at room temperature for 72 hours. The resulting suspension was filtered, which resulted in 230 mg of white solid. The filtrate was evaporated and the residue was treated with ether. After filtering the undissolved substance, another 520 mg of product were obtained. Yield 750 mg of amide (compound No. 1. Table A) having a melting-point of 256° C.

Example V

To 1.92 g of 1-(3,4,5-trimethyoxyphenyl)-3-hydroxymethyl-3,4-dihydro-pyrido[3,4-b]benzo[b]thiophene (obtained according to preparation b) for starting materials) in 25 ml of acetonitrile is added 1.1 g of benzyl bromide. The mixture is refluxed overnight and then evaporated in vacuo. After triturating the residue with ether, the white solid is disolved in 25 ml of methanol and cooled to −70° C.; 0.5 g of sodium borohydride is added portionwise. After stirring for 1 hour at −70° C.

10 ml of aceton is added. The mixture is warmed to room temperature and stirred for 2 hours. After concentrating in vacuo the residue is brought in dichloromethane and washed with brine. The organic layer is dried over MgSO4 and evaporated in vacuo. The resulting residue is dissolved in 50 ml of acetic acid and hydrogenated over palladium or charcoal. The catalyst is filtered off and the filtrate is evaporated in vacuo. The residue is washed with 5% of sodium bicarbonate and purified by flash chromatograph with 2% of methanol in dichloromethane. By this method compound no 18 of table A is obtained having a melting point of 148° C.

a) Preparation of a starting compound as used in Example I

To a suspension of 4 g of L-tryptophan ethyl ester in 75 ml of toluene is added 3.5 g 3.5 dimethoxy benzaldehyde. The reactron mixture is refluxed for 8 hours and then 2 ml of trifluoroacetic acid is added. The mixture is refluxed again for 24 hours. After evaporation in vacuo, the residue is dissolved in 150 ml of methylene chloride and washed with sodium bicarbonate and water. The solution is dried over MgSO4 and evaporated in vacuo. The so obtained mixture of cis and trans isomers is separated by flash chromatography with methylene chloride: methanol 99:1 as an eluent. By this method two fractions were obtained. Fraction 1:2.5 g the cis isomer, melting point 155° C. and fraction 2:2.2 g of the trans isomer, melting point 65° C. These isomers were reduced to the corresponding amino alcohols as described in example 1.

b) Preparation of a starting compound as used in Example V 30 ml of phosphoroxy trichloride is added to a suspension of 10.08 g of ethyl-α-(3.4,5-trimethoxybenzoylamino-β-(benzofuran-3-yl)propionate in 60 ml of acetonitrile. The reaction mixture is refluxed for 16 hours and evaporated in vacuo. The residue is taken up in methylene chloride and washed with 5% of sodium bicarbonate solution until neutral. The solution is dried over MgSO4 and evaporated in vacuo. The residue is taken up in methanol and stirred with 10 g of potassium carbonate for 1 hour. The reaction mixture is pourred into water and extracted with methylene chloride. After drying over MgSO4 and evaporation in vacuo 7.22 g of the compound (5) is obtained, wherein $Z_1$ in symbol $Z_3$ is the group $Z_5$, A is oxygen, and $R = R_1 = R_2 = R_{13} = H$, i.e. 1-(3,4,5-trimethoxyphenyl-3-hydroxymethyl3,4-dihydro-pyrido[3,4-b]benzo[b]furan, having a meltingpoint of 110° C.

We claim:
1. A compound of the formula

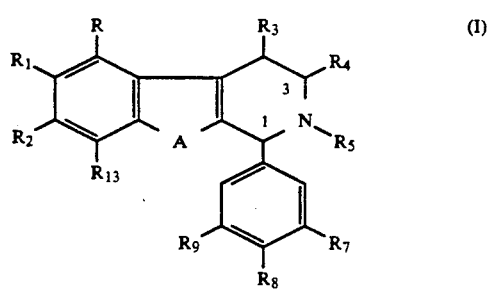

wherein
R, $R_1$ and $R_2$ are hydrogen;

$R_3$ is hydrogen or hydroxy;

$R_4 + R_5$ together form a group of the formula $-C(R_{11})_2-X-Z$, wherein $R_{11}$ is hydrogen or both groups $R_{11}$ together represent a double-bonded keto oxygen atom, X is oxygen or a group $NR_{14}$, wherein $R_{14}$ is hydrogen or alkyl having 1-4 C-atoms, and Z is bound to the $R_5$-substituted ring nitrogen atom and is a group 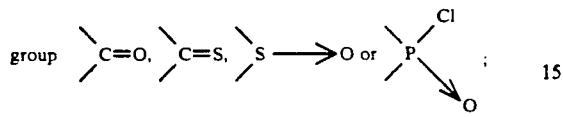;

$R_7$ and $R_9$ independently of each other are hydrogen or alkoxy having 1-4 C-atoms, trifluoromethyl or halogen;

$R_8$ is hydrogen, alkoxy or alkanoyloxy having 1-4 C-atoms, hydroxy, halogen or benzyloxy;

A is oxygen, sulfur or a group $NR_6$, and $R_6$ and $R_{13}$ independently of each other are hydrogen or methyl; or a salt thereof with a pharmaceutically acceptable acid.

2. A compound according to claim 1 wherein
R, $R_1$, $R_2$, $R_3$ and $R_{13}$ are hydrogen;
$R_4$ and $R_5$ are

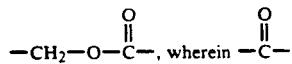, wherein $-\overset{O}{\underset{\|}{C}}-$ is bonded to the nitrogen;
$R_7$, $R_8$ and $R_9$ are $OCH_3$; and
A is

NH.

3. A composition having cytostatic properties, comprising a cytostatically effective amount of a compound as claimed in claim 1 as an active substance and a pharmaceutically acceptable carrier.

* * * * *